United States Patent [19]

DiLeo et al.

[11] Patent Number: 4,728,430

[45] Date of Patent: Mar. 1, 1988

[54] DIAFILTRATION METHOD

[75] Inventors: Anthony J. DiLeo, Westford; Gastón de los Reyes, Framingham; Lisa M. Waranch, Sudbury, all of Mass.

[73] Assignee: Millipore Corporation, Bedford, Mass.

[21] Appl. No.: 828,105

[22] Filed: Feb. 10, 1986

[51] Int. Cl.$^4$ .............................................. B01D 13/00
[52] U.S. Cl. ................................... 210/639; 210/641; 210/651
[58] Field of Search ............... 604/5, 6; 210/257.2, 210/259, 295, 321.1, 433.2, 639, 641, 651, 927

[56] References Cited

U.S. PATENT DOCUMENTS

| | | | |
|---|---|---|---|
| 4,191,182 | 3/1980 | Popovich et al. | 210/651 X |
| 4,215,688 | 8/1980 | Terman et al. | 604/5 |
| 4,223,672 | 9/1980 | Terman et al. | 604/5 |
| 4,350,156 | 9/1982 | Malcheskey et al. | 604/6 |
| 4,350,594 | 9/1982 | Kawai et al. | 210/259 X |
| 4,397,747 | 8/1983 | Ikeda | 210/641 |

FOREIGN PATENT DOCUMENTS

WO84/00112  1/1984  PCT Int'l Appl.

OTHER PUBLICATIONS

Shettigar et al., "Continuous Enrichment of Albumin in Relation to Globulins in Plasma", *Artificial Organs*, May (1982), pp. 163–168.

*Primary Examiner*—Richard V. Fisher
*Assistant Examiner*—W. Gary Jones
*Attorney, Agent, or Firm*—Andrew T. Karnakis; Paul J. Cook

[57] ABSTRACT

A process and apparatus is provided for separating whole blood from a patient into a cellular component and a plasma component and for separating the plasma component into a high molecular weight plasma fraction and a low molecular weight plasma fraction and wherein anticoagulant is added to the whole blood and a physiologically acceptable liquid diluent is added to the plasma component. The rate of addition of the diluent is governed by the following equation:

$$Q_D = \frac{\alpha(1 - h_o)}{\alpha(1 - h_o) + 1} Q_{Pl}\left[(R'' - 1) + \sigma R''\left(\frac{1}{R} - 1\right) + \left(\frac{1}{x} - \frac{\sigma R''}{R}\right)\exp\left(-\frac{R}{R-1}\ln[1 + (R-1)\tau]\right)\right] - \frac{Q_{Pl}}{\alpha(1 - h_o) + 1},$$

called Equation 1.

4 Claims, 6 Drawing Figures

EXTRACORPOREAL CIRCUIT

FIG. 1

INCREASE IN PROTEIN CONCENTRATION
IN RECIRCULATION LOOP AS A FUNCTION OF
VOLUMES EXCHANGED: CLOSED RECIRCULATION

FIG. 2 EXTRACORPOREAL CIRCUIT

FIG. 5

DIAFILTRATION METHOD

BACKGROUND OF THE INVENTION

This invention relates to a diafiltration method and apparatus for separating a whole blood into its cellular component and its plasma component and further separating the plasma component to isolate plasma components such as those components that cause disease.

Diafiltration comprises an ultrafiltration process wherein a liquid composition is separated utilizing a membrane into a stream containing solute retained by the membrane (retentate stream) and a second stream containing solutes which pass the membrane (permeate stream). In the diafiltration process, the retentate stream is recycled to the separation membrane after a diluent has been added. In constant volume batch diafiltration the rate of diluent addition is equal to the flow rate of the permeate stream and the retentate volume remains constant.

Membrane plasmapheresis can be employed to remove large molecular species of proteins in the plasma that cause disease such as immunologically based diseases or other disease states resulting from excessive concentrations of pathogenic plasma proteins. Presently available processes include a first step wherein blood removed from a patient is separated into its cellular component and its plasma component. The cellular component is recirculated to the patient while the plasma component is treated further to separate a large molecular fraction having a molecular weight above about 70,000 daltons which fraction contains the disease causing protein fraction. The relatively low molecular weight fraction contains proteins required by the patient such as albumin also is recirculated to the patient. The separation of the high nolecular weight plasma fraction from the low molecular weight plasma fraction is accomplished with an ultrafiltration membrane having a pore size that allows passage of the low molecular weight fraction while retaining the high molecular weight fraction.

During the extracorporeal treatment of the plasma, the passage of protein and albumin through the membrane is significantly reduced as the concentration of the rejected high molecular weight fraction increases. This occurs since the general mode of operation is to recirculate the high molecular weight fraction to a reservoir wherein it is admixed with incoming fresh plasma and a diluent such as saline. The resulting composition then is recirculated to the ultrafiltration membrane. The diluent is added to reduce the concentration of the high molecular weight fraction in the recirculation loop and thereby reduce plugging of the membrane pores. If too little diluent is employed undesired pore plugging results. If excessive diluent is employed a larger ultrafiltration membrane area is required and the stream recirculated in the patient will contain undesirably high concentrations of the diluent. Consequently, presently available ultrafiltration modules operate at low separation efficiencies and at high recirculation rates (high tangential shear rates). Also, presently available systems operate at fluxes sufficiently low to accommodate the concentration build up in the recirculation loop and therefore require a large excess of ultrafiltration membrane area.

Smeby et al in PCT international application number PCT/NO 83/00025 disclose a process for separating a plasma fraction into a high molecular weight fraction and a low molecular weight fraction. The process utilizes an extracorporeal cascade filtration device having a recycle loop which includes a variable volume reservoir and utilizes a large dilution in the recycle loop. The process is designed and operated to respond dynamically to the lowering flux associated with accumulated protein in this reservoir by lowering the permeate volumetric flow rate from the primary filter (which separate blood cellular components from blood plasma components) to match the maximum flow rate achievable from the secondary plasma filter (which separates the high molecular weight plasma fraction from the low molecular weight plasma fraction) which flow rate is reduced as flux decreases. An additional third filter which is completely retentive of all proteins is included in the apparatus to (a) concentrate the albumin recovered at low concentration (resulting from excess membrane area) and (b) return the water removed by the filter to the recirculation reservoir thereby to dilute the accumlated protein and thereby recover flux. The system is undesirable since it requires excessive membrane area and controls flux by reducing volumetric flow rates rather than by utilizing a mode of operation which permits maintaining higher flux.

U.S. Pat. No. 4,350,156 to Malchesky et al discloses a process for treating plasma to remove macromolecules having a molecular weight greater than about 70,000 daltons in order to provide therapeutic treatment of various disease states. Whole blood is first separated into its cellular components and its plasma component. The plasma component is cooled, filtered to retain the macromolecules while permitting passage of the smaller molecular component such as albumin through the filter. The cellular components and the plasma components passed through the filter then are recycled to the patient. Prior to being filtered, the plasma is cooled to a temperature of about 10° C. The primary problem with this mode of operation is that the membrane filter quickly becomes clogged which results in a low percentage of albumin being passed through the filter for recycling to the patient. This requires that make up albumin be supplied to the patient during the plasmapheresis treatment.

U.S. Pat. No. 4,350,594 to Kawei et al discloses a two step blood treatment process wherein whole blood is separated into its plasma component and its cellular component in a first step. In the second step, the plasma component is separated into a high molecular weight fraction and a low molecular weight fraction. The low molecular weight fraction and the cellular component are recirculated to the patient. This patent discloses that substitute fluids such as saline, anticoagulant or the like are introduced into the system at a rate equal to the rate of removal of the high molecular weight plasma fraction. There is no disclosure of the use of a recirculation loop to recirculate the high molecular weight fraction to the second separation step in order to improve the efficiency of the plasma separation. As a result, large amounts of albumin are lost with the discarded high molecular weight fraction particularly after the apparatus has been in use and the membrane utilized to separate the plasma fraction gradually has become plugged. Accordingly, albumin must be supplied independently from a source other than the patient which increases the risk of the introduction of disease and possible adverse immunological reaction period. U.S. Pat. No. 4,191,182 to Popovich et al discloses a process for tr atment whole blood wherein the cellular components are separated from the plasma utilizing an ultrafiltration membrane. A portion of the cellular components are recycled for admixture with incoming whole blood in order to improve the separation efficiency of the membrane. This patent does not disclose any particular means for further fractionating the plasma component.

U.S. Pat. Nos. 4,215,688 and 4,223,672 to Terman et al discloses a method and apparatus for treating whole blood which includes separating whole blood into its cellular component and its plasma component and subsequently treating the plasma component by contacting it with an immunoadsorbant in order to remove a particular antigen, antibody or antigen-antibody complex from the blood. Neither of these patents discloses separating the plasma component into a high molecular weight fraction and a low molecular weight fraction.

It would be desirable to provide a diafiltration system wherein the means for adding diluent to the high molecular weight fraction in the recirculation loop promotes efficient separation without the need for excessive separation membrane area or excessive dilution. Furthermore, it would be highly desirable to provide a method for effecting plasmapheresis which includes a step of fractionating the plasma fraction into a high molecular weight fraction and a low molecular weight fraction whereby the plasma membrane filtration surface area can be minimized. Also, it would be desirable to provide such a process and apparatus whereby the flux across the plasma separation membrane as well as the albumin permeation through the membrane could be accurately predicted and controlled so that the high molecular weight protein removal can be accurately estimated and the albumin make up, if any, can be accurately estimated.

SUMMARY OF THE INVENTION

This invention is based upon the discovery that by controlling the rate of dilution of a blood plasma component being fractionated so that the concentration of at least one high molecular weight species retained by the membrane is essentially constant, unexpected advantages are obtained. As a result of operating in this manner the membrane surface area can be minimized, plasma dilution can be controlled at low levels so that the patient is not overloaded with excess liquids and efficient separation of high molecular weight plasma components from low molecular weight plasma components can be effected. This result is achieved by adding the diluent to the plasma component at a flow rate which diminishes exponentially with time.

The whole blood to which anticoagulant has been added is first separated into its cellular component and its plasma component. The plasma component subsequently is separated into a high molecular weight fraction and a low molecular weight fraction and at least a portion of the low molecular weight fraction is admixed with the cellular component from a first separation step and returned to the patient. The plasma component is separated into a high molecular weight fraction and a low molecular weight fraction in a second separation step which is comprised of a membrane separation device and a recirculation circuit. The recirculation circuit comprises a portion of the separated high molecular weight plasma fraction which is recirculated to an expandable reservoir and then from the reservoir back to the second separation step. The diluent stream is added to this expandable recirculation circuit at the flow rate which diminishes exponentially with time. The volumetric flow rates from the patient, from the separation steps, and in the recirculation circuit as well as the rates of anticoagulant flow and diluent flow into the system are controlled to produce the desired advantages set forth above. The shear rate across the membrane in the second separation step is sufficiently high to prevent the formation of a molecular boundary layer at the membrane surface.

DESCRIPTION OF SPECIFIC EMBODIMENTS

The present invention will be described in detail hereinafter with reference to a plasmapheresis method and apparatus wherein an albumin-rich stream and the cellular component of blood are recycled to a patient. The present invention is also applicable to separating whole blood into a cellular component, a high molecular weight plasma component and a low molecular weight plasma component and wherein a desired constituent of blood, such as Factor VIII is recovered either simultaneously or at some later time by an appropriate recovery process such as by immunoadsorption.

In accordance with this invention the volumetric flow rates of the diluent liquid streams created in the system of this invention is regulated in order to maintain the concentration of a desired (or selected) species at an essentially constant level in the recirculation circuit. The equation set forth below represents the ideal approximation of the diluent flow rate which minimizes membrane surface area, avoids the use of excess diluent and maintains high separation efficiency. It is to be understood that in accordance with this invention, the diluent flow rate, $Q_D$ will vary plus or minus 10 percent the $Q_D$ calculated from Equation 1. This is due to the normal variable flow rates obtained with available apparatus such as the pumps, the conduits which may become partially blocked during use and like effects. By the phase "diluent flow rate" as used in the claims and specification herein is meant the $Q_D$ calculated from Equation 1, plus or minus 10%.

When operating so that the rejection coefficients of all species remains constant through the procedure, the flow rate of the diluent liquid stream is defined by the following relationships:

$$Q_D = \frac{\alpha(1-h_o)}{\alpha(1-h_o)+1} Q_{P1} \left[ (R''-1) + \sigma R'' \left( \frac{1}{R} - 1 \right) + \left( \frac{1}{\chi} - \frac{\sigma R''}{R} \right) \exp\left( -\frac{R}{R-1} \ln[1+(R-1)\tau] \right) \right] - \frac{Q_{P1}}{\alpha(1-h_o)+1}$$

Figure 2:
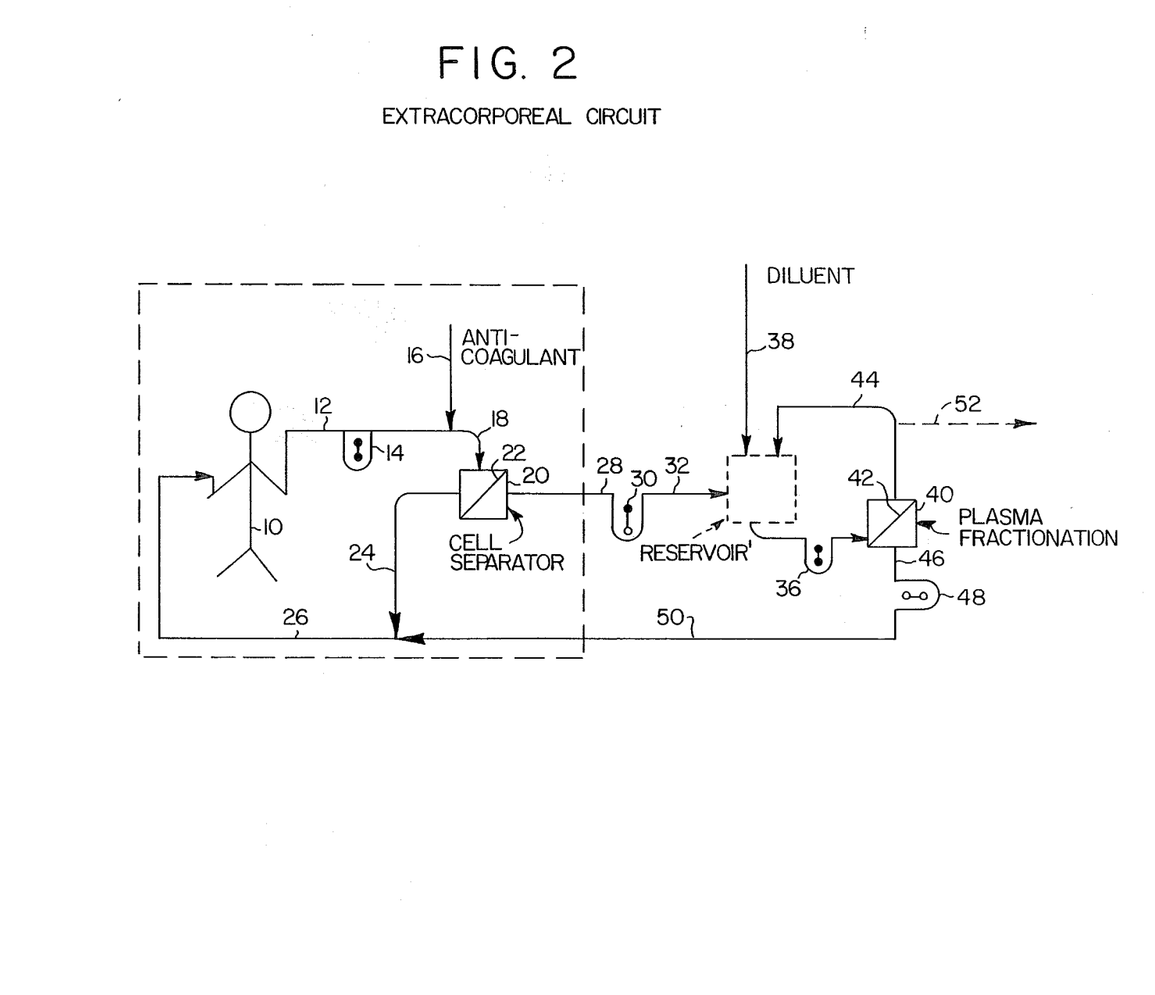
FIG. 2 is a schematic view of a plasmapheresis and plasma separation system utilized in the present invention.

Equation 1

Where (referring to FIG. 2)

$Q_D$ = flow rate of diluent (stream 38)
$Q_{P1}$ = plasma flow rate (stream 28) withdrawn from the first separation device separator 20
$\alpha$ = "anti-coagulant ratio": ratio of the flow rate of whole blood withdrawn from the patient (stream 12) to the anticoagulant flow rate (stream 16)
$h_o$ = patient hematocrit (fractional)
R = "patient replacement ratio": the ratio of total flow rate returned to the patient (stream 26) to total flow rate withdrawn (stream 12)
For isovolemic operation R=1
R" = secondary system "replacement ratio": the ratio of permeate flow rate from secondary (stream 46) to plasma flow rate being processed, which is equal to $$\frac{\alpha(1-h_o)}{\alpha(1-h_o)+1} Q_{P1}.$$

$\tau$ = number of plasma volumes processed $$\tau = \frac{\alpha(1-h_0)}{\alpha(1-h_0)+1} \int_0^t \frac{Q_{P1}}{V_0}(t)dt$$

t = procedure time (i.e. elapsed time)
$V_o$ = initial patient plasma volume (at zero time)
$\sigma$ = the sieving coefficient in the second separation device (separator 40) of the species to be held constant The relationship between R and R" is given by $$R'' = R - \frac{1}{\alpha(1-h_o)} \cdot \frac{1-\eta}{\eta}.$$

Equation 2

Where
$\eta$ = filtration efficiency of the primary filter comprising the ratio of flow rate of liquid filtered (stream 28) to flow rate of liquid fed (stream 18).
$\chi$ = ratio of the concentration in the recirculation reservoir of the species selected to be maintained constant (whose sieving coefficient is $\sigma$) to the concentration of this species in the patient at the start of the procedure.

An exponentially decreasing diluent flow rate is required to maintain essentially constant concentration in the recirculation loop to match the decrease in concentration which occurs in the patient with time. Diluent addition at a rate much less than that described in equation 1 would result in the build-up in the concentration of high molecular weight species in a manner similar to that shown in FIG. 1. This results in loss of membrane performance. Diluent added at a rate greater than that described in Equation 1 results in overdilution and excess volume being returned to the patent.

All these equations equally apply to the case in which a waste (or bleed) stream is being withdrawn from the recirculation stream as long as the waste stream is small enough to keep the recirculation reservoir from getting empty or where no waste or bleed stream is being withdrawn.

Figure 3:
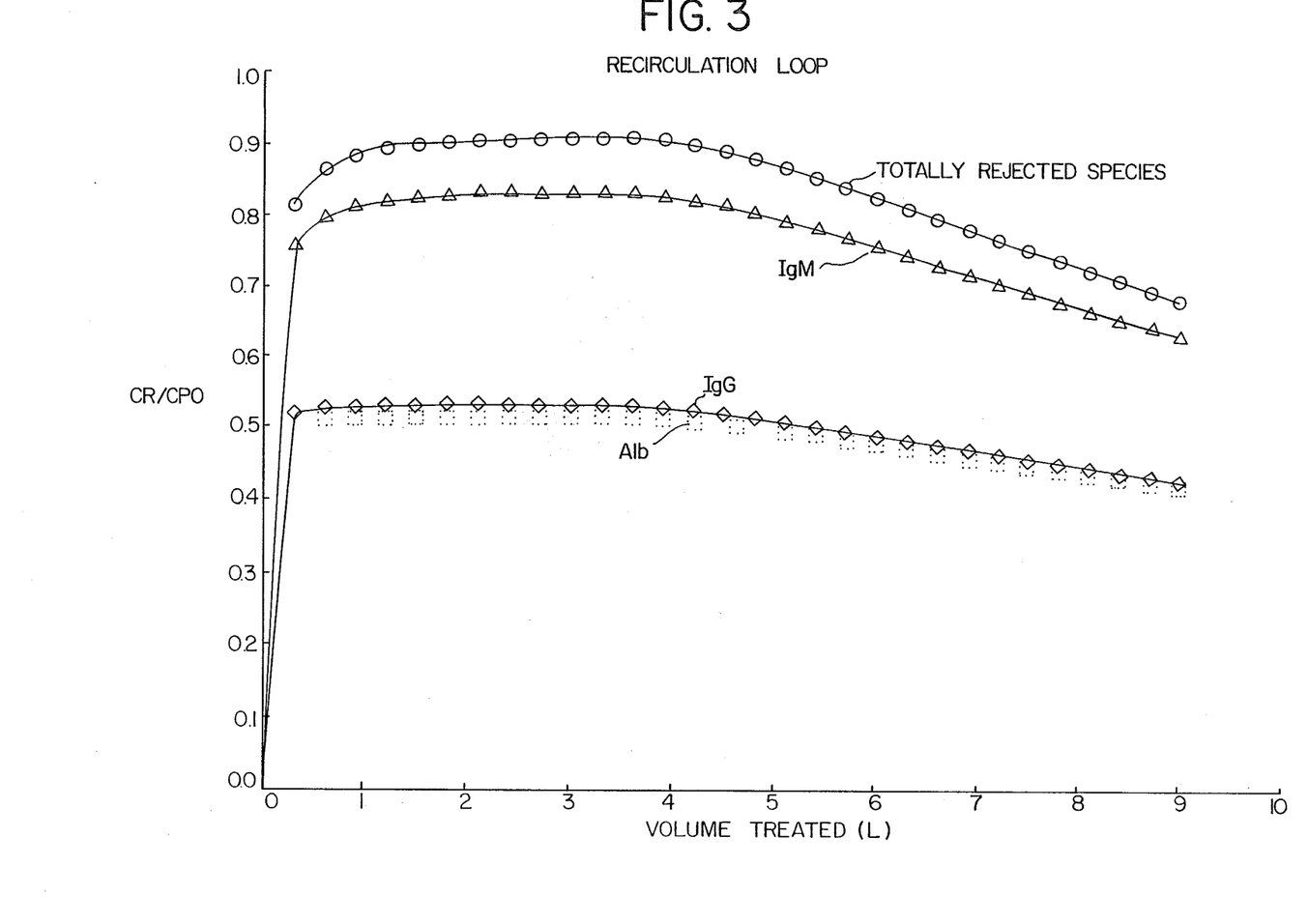
FIG. 3 shows the calculated relative concentration of albumin, totally rejected protein species, IgM and IgG as a function of the volume of the plasma stream treated in the recirculation loop. These results are calculated using Equation 1.

If the process shown in FIG. 2 is operated in accordance with Equation 1 then, as shown in FIG. 3, the concentration of the selected high molecular weight species remains constant as the total volume of plasma processed in the secondary plasma separation step increases.

Referring to FIG. 2, a catheter which communicates with conduit 12 is inserted into the patient 10 in order to pump the blood from the patient 10 by means peristaltic pump 14. An anticoagulant is introduced into the system through conduit 16 into conduit 18. The whole blood containing anticoagulant is introduced into a cell separator 20 such as a centrifuge adapted to separate whole blood into its plasma component and into its cellular component. Any suitable means for separating the whole blood into its plasma component and cellular component can be utilized in the present invention. Typically, plasma separation can be effected by passing the whole blood into contact with a microporous membrane 22 generally having a pore size of about between 0.05 and 1.0 microns, particularly membranes having a pore size of about 0.6 microns. When utilizing the volumetric flow rates defined above, typical pressures across the microfiltration membrane in step 20 are usually between about 10 to about 100 mm Hg.

The cellular blood component is directed through conduits 24 and 26 and reinjected into the patient 10. The plasma component is removed from cell separator 20 through conduit 28 by means of peristaltic pump 30 and passed through conduit 32 and to reservoir 34. A physiologically acceptable diluent is added to the reservoir 34 through conduit 38 at a flow rate that diminishes exponentially with time as set forth above. The mixture of diluent and plasma is removed from reservoir 34 by means of peristaltic pump 36 and directed to a second separation step 40 wherein a low molecular weight plasma fraction is separated from a high molecular weight plasma fraction by means of membrane 42. The high molecular weight plasma fraction is recycled to reservoir 34 by means of conduit 44. The low molecular weight plasma fraction containing albumin is removed from separation step 40 through conduit 46 by means of peristaltic pump 48 and is recycled to the patient 10 by means of conduit 50 and conduit 26. The rate of addition of diluent to reservoir 34 as regulated in accordance with the equations set forth above, and the control of peristaltic pump 30 and 48 regulate the flow rates of the various plasma strength containing streams. In an alternative embodiment of this invention, a bleed stream 52 can be utilized in order to remove a portion of the high molecular weight plasma fraction from the system.

Typical operating conditions for the system shown schematically in FIG. 2 are as follows:

The peristaltic pump 14 is operated in order to effect whole blood removal from the patient at a flow rate between about 20 and about 180 ml/min. The anticoagulant such as heparin, ACD (anticoagulant citrate dextrose), triisodium citrate or a combination thereof typically is added in aqueous solution at a flow rate through conduit 16 usually between about 8% and about 14% of the whole blood flow rate. The pump 30 which effects removal of the plasma fraction from separator 20 generally is operated to effect a flow rate in conduit 28 of about 5 and about 60 ml/min. The pump 48 which effects removal of the low molecular weight plasma fraction generally is operated to effect a flow rate in conduit 50 between about 10 to about 40 ml/min. The addition of the diluent through conduit 38 to reservoir 34 is then added at a rate determined by equations 1–4 an by the amount of albumin return which is desired. For example, when the albumin concentration returned is 50 percent of that initially in the patient, typical flow rates are whole blood in conduit 12 of about 100 ml/min. anticoagulant in conduit 16 of about 10 ml/min., plasma flow rate in conduit 28 of about 30 ml/min., recirculated plasma in conduit 44 of about 1,000 ml/min., low molecular weight plasma fraction in conduit 50 of about 30 ml/min. and flow rate of diluent initially of about 30 ml/min. and gradually to 0 over a time period of about 1.5 hours.

Figure 4:
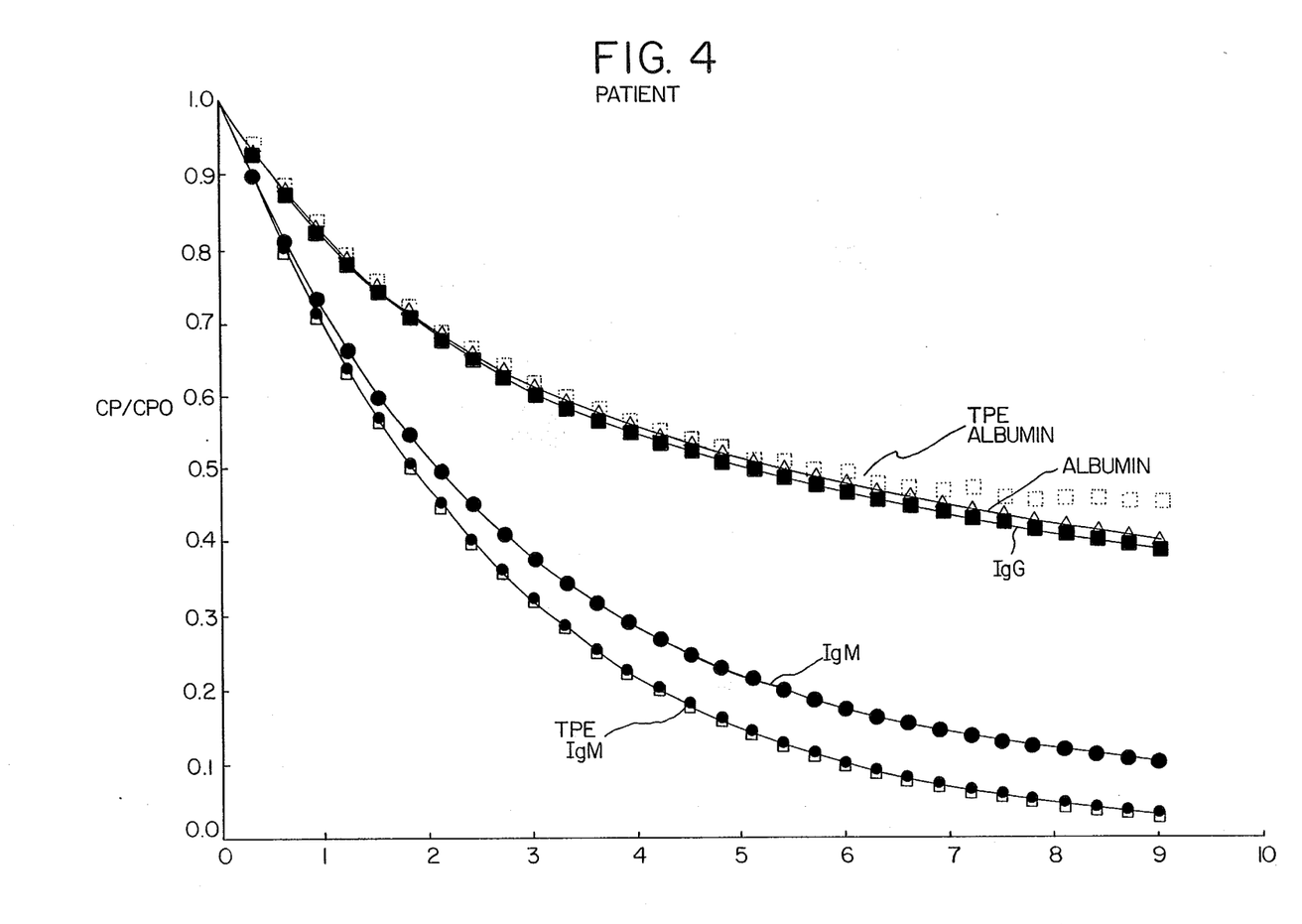
FIG. 4 shows the calculated concentration ratio of the plasma in the patient as a function of plasma volume treated for various protein species.

Theoretical results of the operation of the system shown in FIG. 2 are shown in FIGS. 3 and 4. The system was designed to recover 50 percent of the patient's albumin in accordance with Equation 1 set forth above. As shown in FIG. 3, the albumin in the recirculation loop ranged between 42 percent and 53 percent of the patient's total albumin when 9 liters of blood were treated over a time period of about 5 hours. The corresponding albumin, IgG and IgM concentrations in the patient relative to initial values as shown in FIG. 4. As can be seen, patient's albumin concentration exactly matches that obtained with Total Plasma Exchange (TPE) and 50 percent exogenous albumin return. In addition, the amount of IgM removed from the patient is a maximum which could be removed given a specified albumin recovery for the particular filtration membrane used. The filtration membrane used in the secondary plasma fractionation step was a polyvinylidene fluoride ultrafiltration membrane. The following example illustrates the present invention and is not intended to limit the same.

EXAMPLE 1

Figure 1:
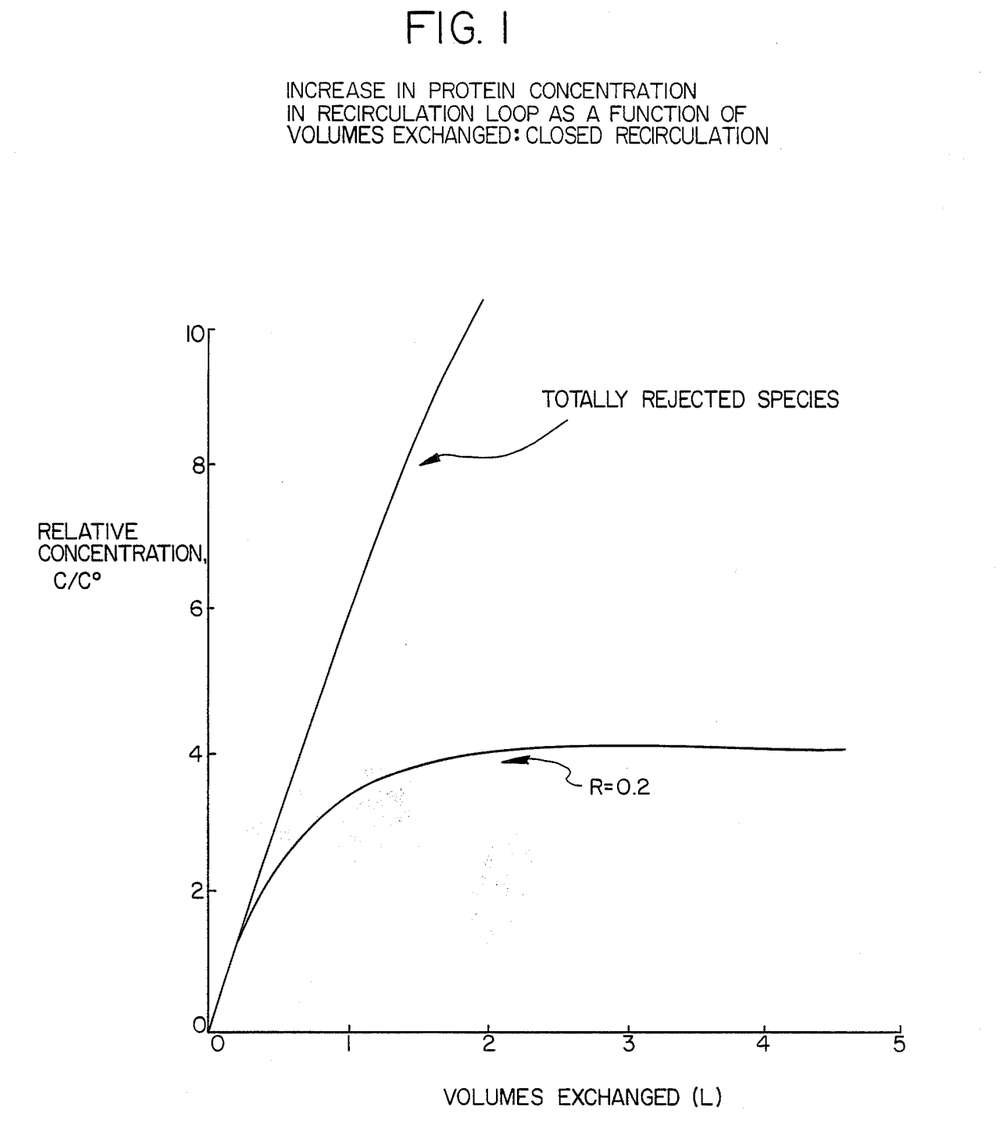
FIG. 1 shows a typical prior art protein concentration increase in the recirculation loop of a plasmapheresis process as a function of plasma volumes exchanged.
Figure 5:
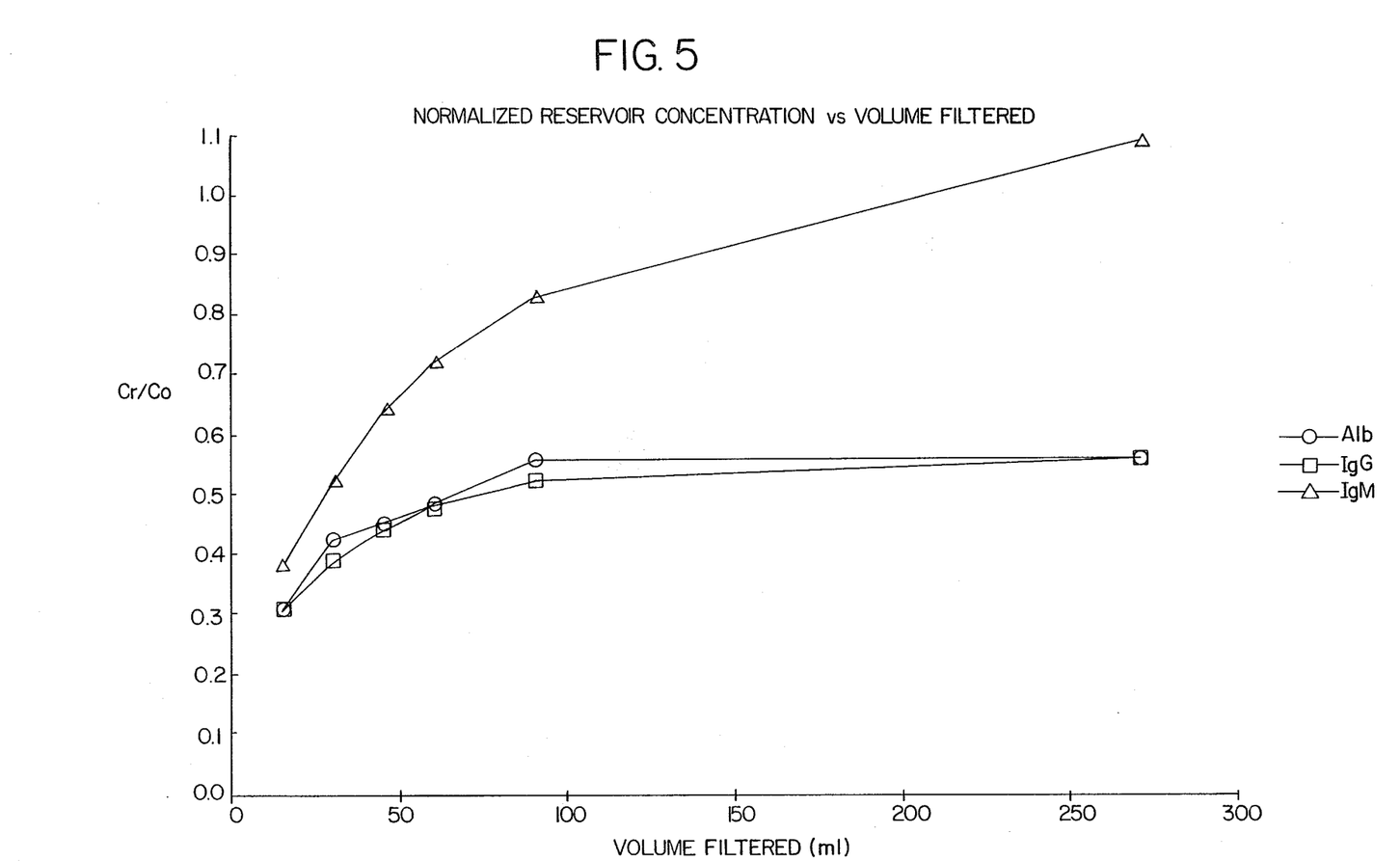
FIG. 5 shows the results of Example 1 where the ratio of retentate concentration vs original concentration of plasma species as a function of plasma volume filtered experimentally measured.
Figure 6:
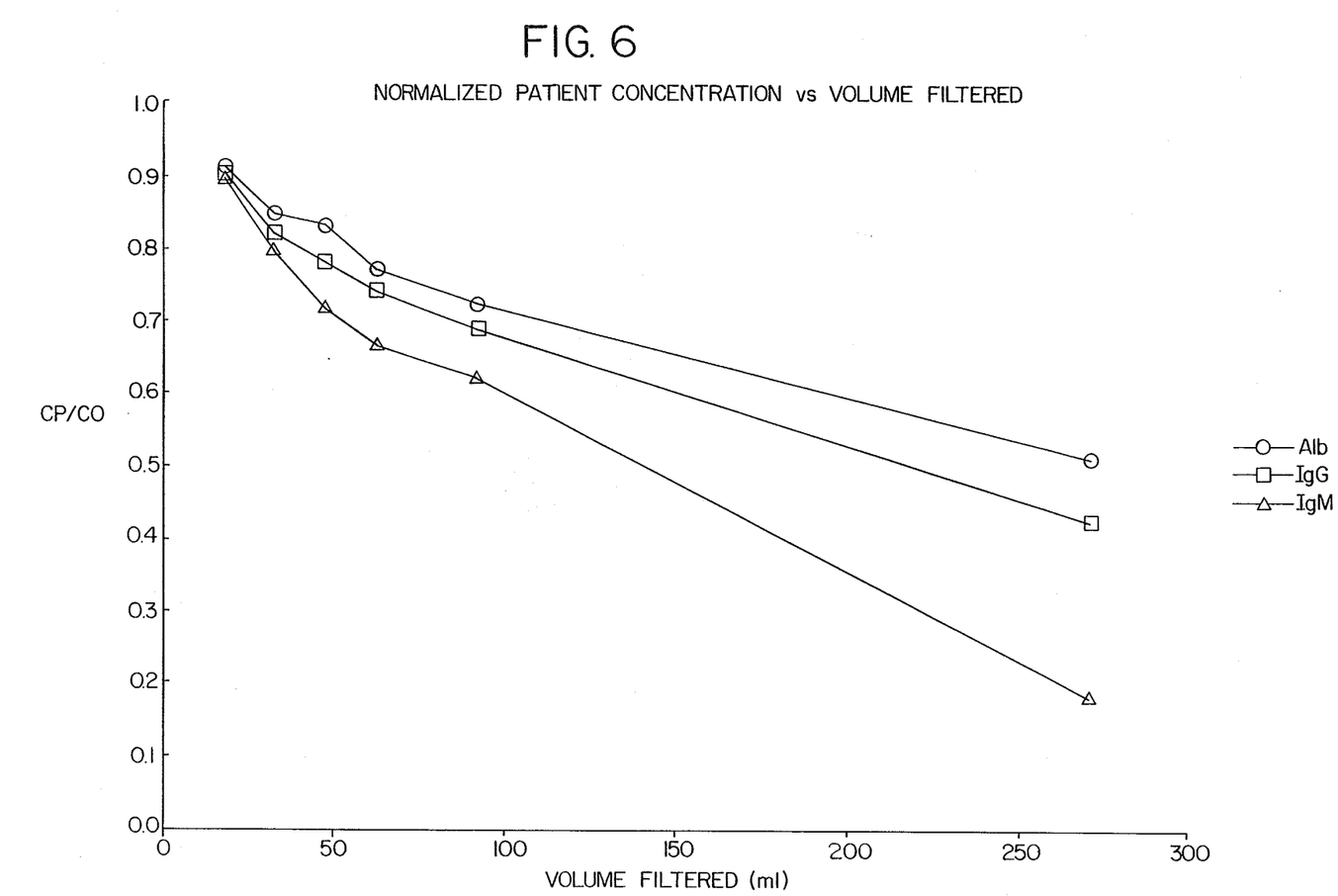
FIG. 6 shows the results of Example 1 where the ratio of permeate concentration vs original concentration of plasma species as a function of plasma volume filtered.

The system shown in FIG. 2 was utilized except that fresh anticoagulated human plasma (150 mls) in a blood bag which replaced the patient and apparatus enclosed by the segmented line 11 of FIG. 1 was used rather than a human patient as the whole plasma source. No cell separator was used and no additional anticoagulant was added. The ultrafiltration module used has a total membrane area of 60 cm$^2$. The flow rate of the diluent stream $Q_D$, is given by the equation 1 and $Q_D = 1.35^{-0.01t}$. The rejection coefficient of albumin in the plasma source ($R_{alb}$) was 0.15. That of IgG ($R_{IgG}$), and IgM (RIgM) were 0.30 and 0.93 respectively. The flow rate returned to the plasma bag ("patient") was 1.5 ml/min. The experimental diafiltration flow rate was selected per equation 1 such that albumin was held constant in the reservoir. As shown in FIG. 5, the albumin concentration was held constant and the IgG concentration was also held constant. The concentration of IgM increased slightly over time. The volume filtered over time was two volumes of the plasma bag. As shown in FIG. 6, the protein concentrations of the original plasma feed decreased as a function of plasma volume filtered (time).

We claim:

1. The process for separating whole blood into a cellular component and a plasma component and for separating said plasma component into a high molecular weight plasma fraction and a low molecular weight plasma fraction consisting essentially of:
    (a) withdrawing whole blood from a patient,
    (b) continuously introducing anticoagulant into whole blood,
    (c) passing the mixture of whole blood and anticoagulant through a first separating means adapted to separating whole blood to form a cellular component and a plasma component,
    (d) adding a physiologically acceptable liquid diluent to said plasma component at a diluent flow rate defined by Equation 1:

Equation 1

$$Q_D = \frac{\alpha(1 - h_o)}{\alpha(1 - h_o) + 1} Q_{P1} \left[ (R'' - 1) + \sigma R'' \left( \frac{1}{R} - 1 \right) + \left( \frac{1}{x} - \frac{\sigma R''}{R} \right) \exp\left( -\frac{R}{R-1} \ln[1 + (R-1)\tau] \right) \right] - \frac{Q_{P1}}{\alpha(1 - h_o) + 1}$$

thereby to form a mixture of said diluent and said plasma component,
    (e) separating said mixture of diluent and said plasma component into a high molecular weight plasma fraction and a low molecular weight plasma fraction,
    (f) recycling at least a portion of said high molecular weight fraction to be admixed with said mixture of diluent and said plasma component, and
    (g) recycling said cellular component and said low molecular weight plasma component directly to said patient.

2. The process of claim 1 wherein 100 percent of the high molecular weight plasma fraction is recycled to be admixed with said mixture of diluent and said plasma component.

3. The process of claim 1 wherein said plasma component is separated into a high molecular weight plasma fraction and a low molecular weight plasma fraction by passing said plasma component into contact with an ultrafiltration membrane.

4. The process of claim 1 wherein the rate of addition of said liquid diluent is at least partially controlled by recycling between about 50–60 percent of the albumin in the original whole blood to the patient.

* * * * *